United States Patent
Mann et al.

(10) Patent No.: US 6,683,709 B2
(45) Date of Patent: Jan. 27, 2004

(54) PHOTOCHROMIC PYRAN COMPOUNDS

(75) Inventors: Claudia Mann, Munich (DE); Udo Weigand, Munich (DE); Manfred Melzig, Wessling (DE)

(73) Assignee: Rodenstock GmbH, Munich (DE)

( * ) Notice: Subject to any disclaimer, the term of this patent is extended or adjusted under 35 U.S.C. 154(b) by 0 days.

(21) Appl. No.: 10/067,529

(22) Filed: Feb. 7, 2002

(65) Prior Publication Data

US 2002/0169315 A1 Nov. 14, 2002

Related U.S. Application Data

(63) Continuation of application No. PCT/EP01/06392, filed on Jun. 6, 2001.

(30) Foreign Application Priority Data

Jun. 7, 2000 (DE) .......................................... 100 27 763

(51) Int. Cl.[7] .................... C07D 493/10; C07D 495/10; G02B 5/23
(52) U.S. Cl. ........................... 359/241; 549/58; 549/60; 549/331; 549/345; 549/330; 544/6; 544/70; 544/150; 544/230; 544/15; 544/18; 548/357.5; 548/407; 548/147; 548/300.7; 548/216; 252/586; 311/96
(58) Field of Search ............................. 549/58, 60, 331, 549/345, 330; 544/6, 70, 150, 230; 546/15, 18; 548/357.5, 407, 147, 300.7, 216; 252/586; 311/96; 359/241

(56) References Cited

FOREIGN PATENT DOCUMENTS

| | | |
|---|---|---|
| DE | 19902771 | 5/2001 |
| EP | 1054010 | 11/2000 |
| EP | 1116723 | 7/2001 |

OTHER PUBLICATIONS

Copy of Search Report.

Primary Examiner—Mark L Berch
Assistant Examiner—Kahsay Habte
(74) Attorney, Agent, or Firm—Crowell & Moring LLP

(57) ABSTRACT

Photochromic pyran compounds and their use in synthetic resin objects of all types, especially for ophthalmic applications, particularly spiro compounds having a fluorene structure derived from naphthopyrans, which are known as spirofluorenopyrans. By introducing respectively only one strongly electron donating or withdrawing group at specific positions in the periphery of the pyran dye, photochromic compounds obtained which in the excited state are distinguished by an expanded color spectrum, while simulataneously offering comparably good bleaching rates and good durability.

10 Claims, 2 Drawing Sheets

Figure 1:
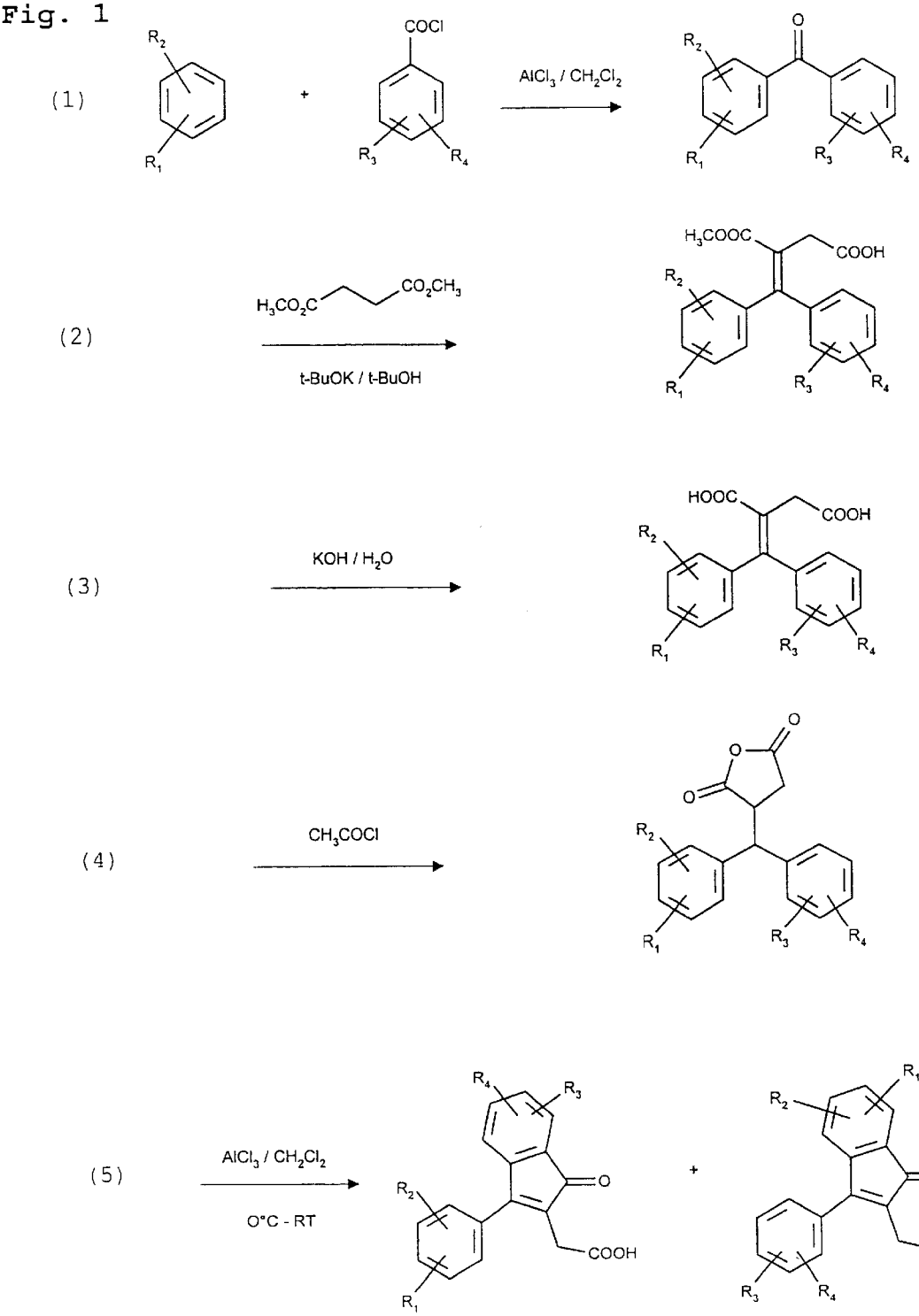

Fig. 1 Continuation
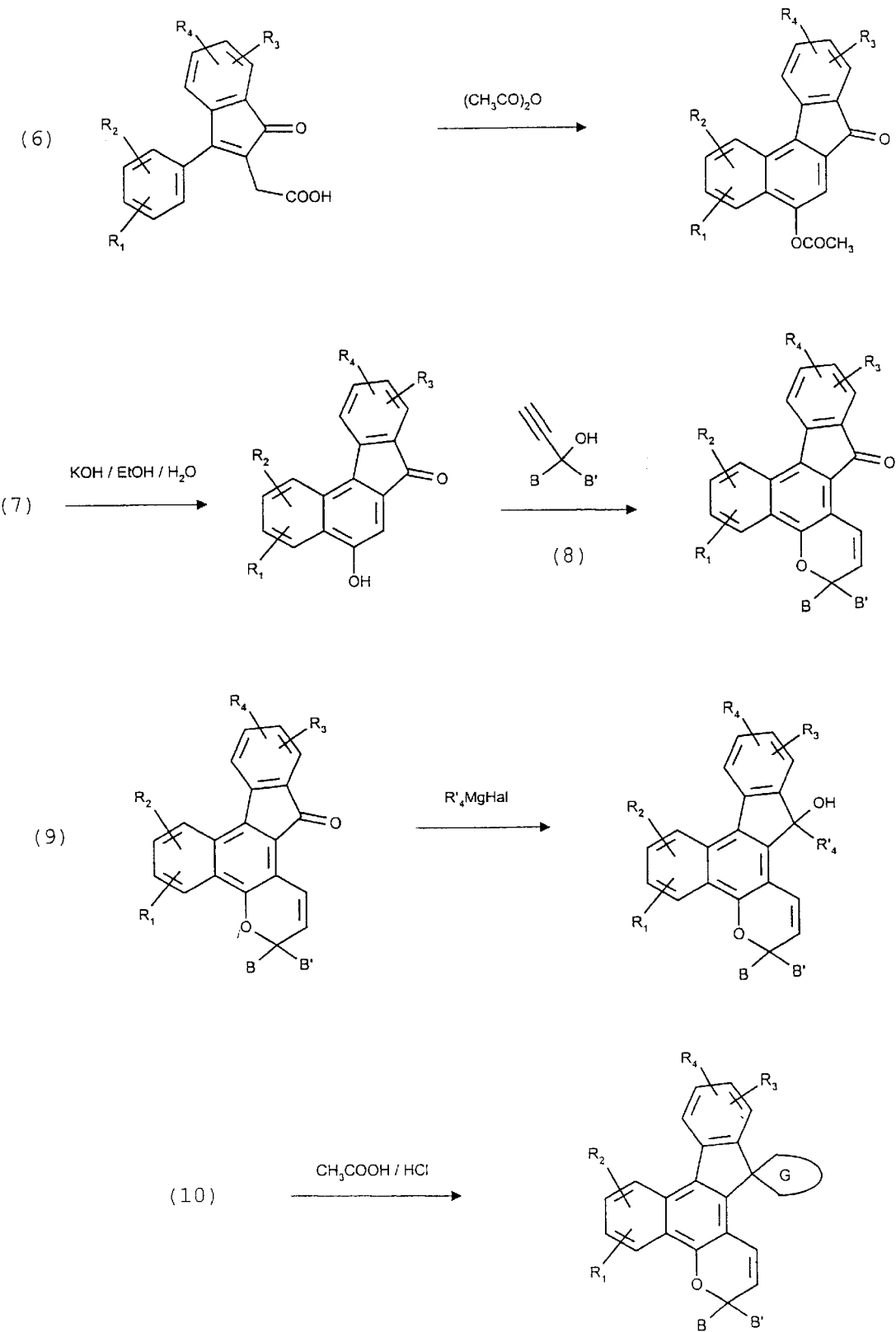

PHOTOCHROMIC PYRAN COMPOUNDS

CROSS REFERENCE TO RELATED APPLICATIONS

This application is a continuation of international patent application no. PCT/EP01/06392, filed Jun. 6, 2001, designating the United States of America, the entire disclosure of which is incorporated herein by reference. Priority is claimed based on Federal Republic of Germany patent application no. DE 100 27 763.2, filed Jun. 7, 2000.

BACKGROUND OF THE INVENTION

The present invention relates to specific photochromic pyran compounds and their use in synthetic resin objects (i.e., plastic objects) of all types, especially for ophthalmic applications. In particular, the present invention relates to spiro compounds having a fluorene structure derived from naphthopyrans, which are known as spirofluorenopyrans. According to the invention, introducing, respectively, only one strongly electron donating or withdrawing group at specific positions in the periphery of the pyran dye yields photochromic compounds that in the excited state are distinguished by an expanded color spectrum, i.e., by a hypsochromic or bathochromic shift of the longest-wave absorption maximum. At the same time, these compounds offer comparably good bleaching or fade rates and good performance in the durability test.

Various classes of dyes that reversibly change their color when irradiated with light of certain wavelengths, particularly sunlight, are known in the art. This is due to the fact that these dye molecules change into an excited colored state when supplied with energy in the form of light. When the energy supply is interrupted, they leave this state again and return to their colorless or at least hardly colored normal state. These photochromic dyes include, for instance, the naphthopyrans, which have already been described in the prior art with various substituents.

Pyrans, especially naphthopyrans and larger ring systems derived therefrom, are photochromic compounds that even today are the subject of intensive investigations. Although a patent application was filed for them as early as 1966 (U.S. Pat. No. 3,567,605), it was not until the nineties that compounds that appeared suitable for use in eyeglasses were developed.

The prior art 2H-naphthopyrans derived from 1-naphthols as well as their higher analogue derivatives obtained by annellation are connected with drawbacks, however, and when used in sunglasses, substantially affect the wearing comfort of the glasses wearer. On the one hand, the prior art dyes frequently do not have sufficiently long-wave absorption in the excited as well as in the unexcited state. This causes problems also in combinations with other photochromic dyes. On the other hand, they are also often excessively temperature sensitive with respect to darkening, and brightening is simultaneously too slow. In addition, the described dyes have an insufficiently long service life. Consequently, this type of sunglasses is not adequately durable. The latter is noticeable in their rapidly deteriorating performance and/or strong yellowing.

By introducing a spirofluorene skeleton as described in German patent applications DE 198 24 278 or DE 199 02 771, photochromic compounds with correspondingly improved properties have been provided. However, their longest-wave absorption maximum in the excited state lies in a very narrow wavelength range of 570 nm to 620 nm. As a result, for instance, green sunglasses can be obtained only by mixing different photochromic dyes. Since the kinetics of the individual photochromic dyes, however, cannot be completely tuned or matched to one another in these dye mixtures, the occurrence of color differences during darkening and bleaching is unavoidable.

SUMMARY OF THE INVENTION

It is an object of the invention to provide novel photochromic pyrans, which are to be distinguished by a broader color spectrum in the excited state than is available in prior art compounds.

Another object of the invention is to provide photochromic compounds which have comparably good kinetic properties.

A specific object of the invention is to provide photochromic compounds which combine rapid bleaching rate with excellent durability.

A further object of the invention is to provide photochromic compounds with which It is possible to obtain green sunglasses by using them alone.

These and other objects are achieved in accordance with the invention by providing a photochromic pyran compound corresponding to formula I:

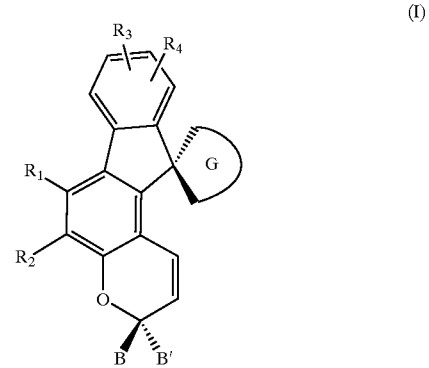

(I)

wherein
$R_1$, $R_2$, $R_3$ and $R_4$ are each independently selected from the group α consisting of the subgroups A, A' and A",
in which
subgroup A consists of hydrogen, ($C_1$–$C_6$) alkyl, ($C_1$–$C_6$) alkoxy, ($C_3$–$C_7$) cycloalkyl which may include one or more heteroatoms, aryl, heteroaryl, benzyl, hydroxy, bromine, chlorine, and fluorine;
in subgroup A', $R_1$ and $R_2$ or $R_3$ and $R_4$ respectively form an —O—$(CH_2)_n$—O— group bound to the aromatic ring, wherein n=1 or 2, and
subgroup A" consists of strongly electron withdrawing groups selected from the group consisting of —$CF_3$, —$NO_2$, —CN and —$SO_2R^5$, wherein $R^5$ is selected from subgroup A, and strongly electron donating groups selected from the group consisting of thio ($C_1$–$C_6$) alkyl, thiophenyl, thiobenzyl, thiomorpholinyl, morpholinyl, piperidinyl, an azacycloheptanyl, piperazinyl, pyrrolidinyl, pyrazolidinyl and unsubstituted, monosubstituted or disubstituted amino, wherein the amine substituents are selected from the group consisting of ($C_1$–$C_6$) alkyl, ($C_3$–$C_7$) cycloalkyl, phenyl and benzyl,
with the proviso that $R^1$ and $R^2$ are bound either directly to the benzopyran unit of formula (I) or via an aromatic or heteroaromatic ring system annellated to the benzopyran unit to form a corresponding naphthopyran unit, and with the further proviso that of $R_1$ and $R_2$, and of $R_3$ and $R_4$, respectively, only one member of each pair is a strongly electron withdrawing group or a strongly electron donating group selected from subgroup A", G including the central Spiro carbon atom represents a saturated or unsaturated ring with 5 to 8 carbon atoms of which at most one may be replaced with a hetero moiety selected from the group consisting of O, S and $NR_5$, where $R_5$ has the meaning given above wherein at least one aromatic or heteroaromatic ring system selected from the group E is annellated to the ring G, wherein group E consists of benzene, naphthalene, phenanthrene, pyridine, quinoline, furan, thiophene, pyrrole, benzofuran, benzothiophene, indole and carbazole, and wherein the ring system optionally may have one or more substituents from the group α defined above;

B and B' are independently selected from one of the groups a), b), c) and d) wherein group a) consists of monosubstituted, disubstituted and trisubstituted aryl selected from the group consisting of phenyl and naphthyl;

group b) consists of unsubstituted, monosubstituted and disubstituted heteroaryl selected from the group consisting of pyridyl, furanyl, benzofuran-2-yl, benzofuran-3-yl, thienyl, benzothieno-2-yl, benzothieno-3-yl or julodinyl;

wherein the substituents of the aryl or heteroaryl in a) and b) are selected from the group consisting of hydroxy, amino, mono($C_1$–$C_6$) alkylamino, di($C_1$–$C_6$) alkylamino, mono- and diphenylamino unsubstituted, monosubstituted or disubstituted on the phenyl ring, piperidinyl, morpholinyl, carbazolyl, unsubstituted, monosubstituted and disubstituted pyrryl, ($C_1$–$C_6$) alkyl, ($C_1$–$C_6$) alkoxy, bromine, chlorine, and fluorine, wherein the substituents of the phenyl or pyrryl are selected from the group consisting of ($C_1$–$C_6$) alkyl, ($C_1$–$C_6$) alkoxy, bromine, chlorine, and fluorine;

group c) consists of structural units having the formulas (V) or (W):

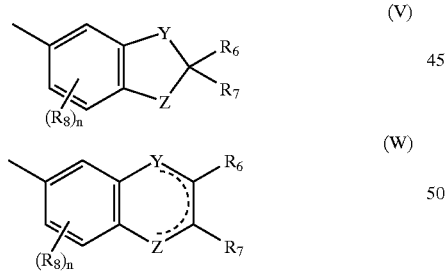

wherein Y and Z are independently selected from the group consisting of O, S, CH, $CH_2$ or $NR_9$, wherein $R_9$ is selected from the group D consisting of ($C_1$–$C_6$) alkyl, ($C_1$–$C_6$) acyl, phenyl and hydrogen; $R_6$ and $R_7$ independently represent hydrogen or ($C_1$–$C_6$) alkyl; $R_8$ is a substituent selected from the subgroup A defined above, and n is 0, 1, 2 or 3;

with the proviso that if Y in formula (V) is $NR_9$, Z is carbon, and in group d) B and B' together form an unsubstituted, monosubstituted or disubstituted fluorene-9-ylidene radical or a saturated hydrocarbon radical, which is $C_3$–$C_{12}$ spiro-monocyclic, $C_7$–$C_{12}$ spiro-bicyclic or $C_7$–$C_{12}$ spiro-tricyclic, wherein the fluorene substituents are selected from the subgroup A.

DETAILED DESCRIPTION OF THE INVENTION

In particular, photochromic pyrans having the following general formula (I) are provided:

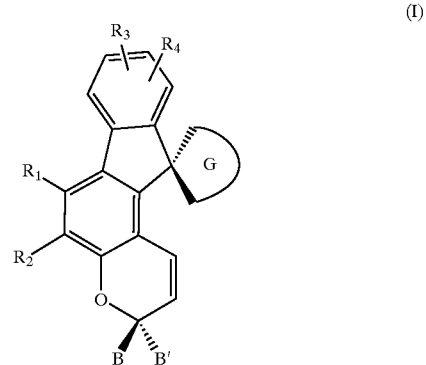

wherein the radicals $R_1$, $R_2$, $R_3$ and $R_4$ each independently represent a substituent selected from the group α comprising the subgroups A: consisting of a hydrogen atom, a ($C_1$–$C_6$) alkyl radical, a ($C_1$–$C_6$) Alkoxy radical, a ($C_3$–$C_7$) cycloalkyl radical, which can have one or more heteroatoms, an aryl radical, a heteroaryl radical, a benzyl radical, a hydroxyl group, bromine, chlorine, and fluorine, and A': according to which the radicals $R_1$ and $R_2$ or $R_3$ and $R_4$ each form an —O—$(CH_2)_n$—O— group bound to the aromatic ring, where n=1 or 2, A": consisting of strongly electron pulling groups, selected from —$CF_3$, —$NO_2$, —CN and —$SO_2R^5$, where $R^5$ is selected from the subgroup A, and strongly electron donating groups selected from a thio($C_1$–$C_6$) alkyl radical, a thiophenyl group, a thiobenzyl group, a thiomorpholine group, a morpholine group, a piperidine group, an azacycloheptane group, a piperazine group, a pyrrolidine group, a pyrazolidine group and an unsubstituted, monosubstituted or disubstituted amino group, wherein the amine substituents may be selected from ($C_1$–$C_6$) alkyl, ($C_3$–$C_7$) cycloalkyl, phenyl, and benzyl, with the proviso that $R^1$ and $R^2$ are bound either directly to the benzopyran unit in accordance with formula (I) or via an aromatic or heteroaromatic ring system annellated thereto while forming a corresponding naphthopyran unit, and with the further proviso that, within the radicals $R_1$ or $R_2$ and/or within the radicals $R_3$ or $R_4$, respectively, only one is a strongly electron pulling group or strongly electron donating group selected from the subgroup A", the structural unit G, including the central spiro carbon atom, represents a saturated and/or unsaturated ring member with 5 to 8 carbon atoms of which at most one may be replaced with a hetero moiety selected from the group consisting of O, S and $NR_5$, wherein the radical $R_5$ is defined as above, wherein at least one aromatic or heteroaromatic ring system is annellated to the ring member, wherein said ring system is selected from the group E consisting of benzene, naphthalene, phenanthrene, pyridine, quinoline, furan, thiophene, pyrrole, benzofuran, benzothiophene, indole and carbazole, and the ring system can have one or more substituents from the group α, preferably from the subgroup A;

B and B' independently are selected from one of the following groups a), b), c) or d) wherein a) consists of monosubstituted, disubstituted and trisubstituted aryl, wherein the aryl is phenyl or naphthyl;

b) consists of unsubstituted, monosubstituted and disubstituted heteroaryl, wherein the heteroaryl is pyridyl, furanyl, benzofuran-2-yl, benzofuran-3-yl, thienyl, benzothieno-2-yl, benzothieno-3-yl or julodinyl;

wherein the substituents of the aryl or heteroaryl radicals in a) and b) are selected from the group consisting of hydroxy, amino, mono($C_1$–$C_6$) alkylamino, di($C_1$–$C_6$) alkylamino, mono- and diphenylamino unsubstituted, monosubstituted or disubstituted on the aromatic, piperidinyl, morpholinyl, carbazolyl, unsubstituted, monosubstituted and disubstituted pyrryl, ($C_1$–$C_6$) alkyl, ($C_1$–$C_6$) alkoxy, bromine, chlorine, and fluorine, wherein the aforementioned aromatic and heteroaromatic ring systems can be substituted with ($C_1$–$C_6$) alkyl, ($C_1$–$C_6$) alkoxy, bromine, chlorine, and fluorine;

c) consists of structural units having the formulas (V) or (W):

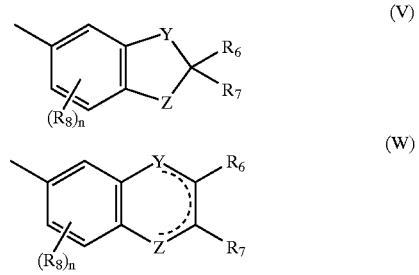

(V)

(W)

wherein

Y and Z independently are O, S, CH, $CH_2$ or $NR_9$, wherein $R_9$ is selected from the group D consisting of ($C_1$–$C_6$) alkyl, ($C_1$–$C_6$) acyl, phenyl and hydrogen, $R_6$ and $R_7$ independently represent hydrogen and/or ($C_1$–$C_6$) alkyl, and $R_8$ is a substituent from the subgroup A, where n is 0, 1, 2 or 3, provided that, if Y in formula (V) is $NR_9$, Z is carbon, or d) B and B' together form an unsubstituted, monosubstituted or disubstituted fluorene-9-ylidene radical or a saturated hydrocarbon radical, which is $C_3$–$C_{12}$ spiro-monocyclic, $C_7$–$C_{12}$ spiro-bicyclic and/or $C_7$–$C_{12}$ spiro-tricyclic, wherein the fluorene substituents are selected from the subgroup A.

Preferably, the structural unit G in the above formula (I), including the central spiro carbon atom, is a substituted or unsubstituted fluorene, xanthene, thioxanthene, phenanthrene or dihydroanthracene unit.

Preferred photochromic compounds are 2H-naphtho[1,2-b]pyrans corresponding to formula II:

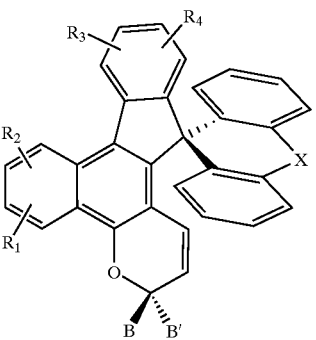

(II)

where $R_1$, $R_2$, $R_3$ and $R_4$ are defined as above and X stands for —$CR'_2$—, —CR'=CR'—, —O—, —S— or a σ single bond, wherein R' is independently selected from the subgroup A, with the aforementioned proviso that within the radicals $R_1$ or $R_2$ and/or within the radicals $R_3$ or $R_4$, respectively, only one is a strongly electron withdrawing group or strongly electron donating group selected from the subgroup A". Preferably, $R_1$ and $R_2$ are attached in the 6-position or 7-position of the naphthopyran unit in accordance with the above formula (II).

In a preferred embodiment, within the radicals $R_1$ or $R_2$ and/or within the radicals $R_3$ or $R_4$ in accordance with the aforementioned formula (I) or (II), respectively, only one is a strongly electron donating group. Preferred strongly electron donating groups include a morpholine group, a piperidine group, an azacycloheptane group, a piperazine group, a pyrrolidine group, a pyrazolidine group and an unsubstituted, monosubstituted, or disubstituted amino group, wherein the amine substituents may be selected from ($C_1$–$C_6$) alkyl, ($C_3$–$C_7$) cycloalkyl, phenyl, and benzyl. In an especially preferred embodiment, within the radicals $R_1$ or $R_2$ and within the radicals $R_3$ or $R_4$, respectively, only one is a strongly electron donating group. In other words, the inventive compound has two spatially separated electron donating substituents in the periphery of the indenobenzopyran or the indenonaphthopyran unit in accordance with formula (I) or (II).

Preferably B and B' in the aforementioned formula (I) or (II) independently are monosubstituted, disubstituted and trisubstituted aryl, wherein the respective aryl is phenyl or naphthyl. The aryl or heteroaryl groups listed in the subgroup A can especially be phenyl, naphthyl, pyrrolyl, pyrazolyl, imidazolyl, imidazolinyl, pyridinyl, pyrimidinyl, pyrazinyl, indolyl, indazolyl, quinolinyl, isoquinolinyl, purinyl, pyrimidinyl, phenanthridinyl, acridinyl, phenazinyl, carbazolyl, thiazolyl or oxazolyl.

Particularly preferred compounds according to the present invention include:

spiro-9-fluorene-13'-[6-(N-morpholinyl)-3-[4-(N-morpholinyl)phenyl]-3-phenyl-indeno[2,1-f]-naphtho[1,2-b]pyran];

spiro-9-fluorene-13'-[6-dimethylamino-3-[4-(N-morpholinyl)phenyl]-3-phenyl-indeno[2,1-f]-naphtho[1,2-b]pyran], and spiro-9-fluorene-13'-[6,11-bis(N-morpholinyl)-3-[4-(N-morpholinyl)phenyl]-3-phenyl-indeno[2,1-f]-naphtho[1,2-b]pyran].

FIG. 1 schematically shows a synthesis scheme for preparing illustrative photochromic compounds according to the invention.

By introducing only one strongly electron donating or withdrawing group selected from the subgroup A" with respect to the respective substituent pairs $R_1$ or $R_2$ and/or $R_3$ or $R_4$, photochromic compounds are obtained, which in contrast to the compounds available in the prior art, particularly those described in published German patent applications DE 198 24 278 or DE 199 02 771, are distinguished by an expanded color spectrum in the excited state, i.e., by a hypsochromic or bathochromic shift of the longest-wave absorption maximum, while simultaneously offering comparably good bleaching rates and good performance in the durability test. Particularly the introduction of only one strongly electron donating group, respectively, such as a morpholine group, a piperidine group, an azacycloheptane group, a piperazine group, a pyrrolidine group, a pyrazolidine group or an unsubstituted, monosubstituted or disubstituted amino group, within the radicals $R_1$ or $R_2$ and/or within the radicals $R_3$ or $R_4$ yields photochromic dyes, which, if used alone, i.e., as the only dye in plastics typically used for eyeglass lenses, impart a blue green to green color impression, which the user perceives as cosmetically attractive.

A cosmetically particularly attractive gray green color impression can be achieved by the additional use of inventive compounds with electron withdrawing substituents. The kinetics are hardly influenced by the different substitution, which is present, respectively, in a position that is very remote from the photochromic reaction center, which is dominated by the unit "G" and the substituents B and B'. In the inventive compounds with electron donating substituents, the bathochromic shift of the longest-wave absorption maximum of the excited form causes a relative absorption hole to appear in the region around 500 nm–550 nm. The green color impression is created by the transmission of precisely this wavelength range. A small addition of an inventive compound with hypsochromically shifted absorption (around approximately 550 nm), i.e., of an inventive compound with electron withdrawing substituents, neutralizes the color impression in the gray-green direction. Since the maximum of the sensitivity of the human eye for day vision (and simultaneously color vision) is at 550 nm, this addition at the same time clearly reduces the transmission toward $V_\lambda$ i.e., higher absorption. This, however, is precisely what is expected or required in sunglasses.

The compounds according to the invention can be used in synthetic resin (i.e., plastic) materials or objects of any type and shape for a wide variety of applications where photochromic behavior is important. A dye according to the present invention may be used alone. However, the scope of the present invention also provides for mixing one or more of the inventive compounds with other photochromic dyes. The photochromic dyes according to the present invention can, for example, be used in lenses, particularly ophthalmic lenses, lenses for eyeglasses of all types, e.g., ski goggles, sunglasses, motor cycle goggles, visors on protective helmets, and the like. The inventive photochromic pyrans can also be used, for example, as sun protection in vehicles and living spaces in the form of windows, baffles, covers, roofs, or the like.

To produce such photochromic objects, the inventive photochromic pyran dyes can be applied to or embedded in a polymer material, such as an organic plastic material, by various methods described in the prior art, for instance in published international patent application no. WO 99/15518.

A distinction is drawn between so-called mass dyeing and superficial dyeing processes. A mass dyeing process comprises, for instance, dissolving or dispersing of the photochromic compound or compounds according to the present invention in a synthetic resin material, e.g., by adding the photochromic compound(s) to a monomer material before polymerization takes place. Another option to produce a photochromic object is to allow the photochromic compound(s) to penetrate the synthetic resin material(s) by dipping the synthetic resin material into a hot solution of the photochromic dye(s) according to the present invention or, for instance, to use a thermotransfer process. The photochromic compound(s) can, for instance, also be provided in the form of a separate layer between adjacent layers of the synthetic resin material, e.g., as part of a polymer film. It is also possible to apply the photochromic compound(s) as part of a coating that is applied to the surface of the synthetic resin material. The term "penetration" should be understood as the migration of the photochromic compound(s) into the synthetic resin material, e.g., through the solvent-supported transfer of the photochromic compound(s) into a polymer matrix, vapor phase transfer or other similar surface diffusion processes. Advantageously, such photochromic objects, e.g., eyeglasses, can be produced not only by means of the usual mass dyeing process but also by means of superficial dyeing. In the latter variant, a surprisingly low migration tendency can be achieved. This is advantageous particularly in subsequent processing steps since, for instance, in an antireflective coating, film peeling and similar defects can be drastically reduced due to the reduced back diffusion in the vacuum.

Overall, based on the inventive photochromic pyran dyes, any compatible (compatible in chemical respects as well as in color) colorations, i.e., dyes, can be applied to or embedded in the plastic material to satisfy both esthetic considerations as well as medical or fashion aspects. The specifically selected dye(s) can consequently vary as a function of the intended effects and requirements.

The inventive photochromic pyrans having the general formula (I), particularly 2H-naphtho[1,2-b]pyrans, or spiro compounds with fluorene structure derived from naphthopyrans, which are known as spirofluorenopyrans, having the general formula (II) can be prepared according to the reaction scheme illustrated in FIG. 1. The substituted or unsubstituted benzophenones used as starting material are either commercially available or can be obtained by conventional Friedl-Crafts acylation (step (1)). Subsequently de Stobbe condensation by means of succinic acid diester in step (2) produces a semi-ester, which is typically obtained as an isomer mixture, provided that the two aromatic rings linked via the keto group are not identical. This semi-ester mixture is subsequently hydrolyzed with aqueous alkali in step (3) to obtain an isomer mixture of the corresponding diacids. Through heating with acetyl chloride in step (4), an isomer mixture of the corresponding cyclic anhydrides is then obtained by dehydration. In step (5) this mixture is reacted with $AlCl_3$, and an intramolecular 5-ring cyclization takes place. In general, the compounds obtained in step (5) crystallize very well and, thanks to their different solubility in benzene, can be readily separated into the two isomers. In step (6), in a reaction with $Ac_2O$, a 6-ring cyclization takes place and a corresponding ester compound is obtained and subsequently subjected to alkaline hydrolysis in step (7). In step (8) this compound is then reacted with a 2-propyne-1-ol derivative to obtain an indeno-annellated naphthopyran derivative. This step and the two subsequent steps are carried out analogously to the conversions with isomeric hydroxyfluorenone derivatives described in published European patent application EP 987,260. In step (9) conversion is effected with suitable Grignard reagents, which in step (10) can be cyclized into the inventive compounds (see FIG. 1).

The foregoing description and examples have been set forth merely to illustrate the invention and are not intended to be limiting. Since modifications of the described embodiments incorporating the spirit and substance of the describe embodiments may occur to persons skilled in the art, the invention should be construed broadly to include all variations falling within the scope of the appended claims and equivalents thereof.

What is claimed is:

1. A photochromic pyran compound corresponding to formula (I) or formula Ia:

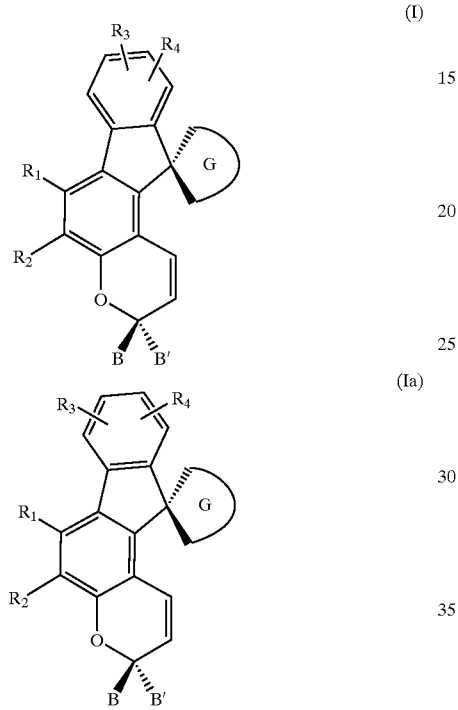

wherein
$R_1$, $R_2$, $R_3$ and $R_4$ are each independently selected from the group α consisting of subgroups A, A', and A",
in which
subgroup A consists of hydrogen, $(C_1-C_6)$ alkyl, $(C_1-C_6)$ alkoxy, $(C_3-C_7)$ cycloalkyl which may include one or more heteroatoms, aryl, heteroaryl, benzyl, hydroxy, bromine, chlorine, and fluorine;
subgroup A' consists of $R_1$ and $R_2$ or $R_3$ and $R_4$ respectively forming an —O—(CH$_2$)$_n$—O— group bound to the aromatic ring, wherein n=1 or 2; and
subgroup A" consists of strongly electron withdrawing groups selected from the group consisting of —F$_3$, —NO$_2$, —CN, and —SO$_2$R$^5$, wherein R$^5$ is selected from subgroup A, an strongly electron donating groups selected from the group consisting of thio $(C_1-C_6)$ alkyl, thiophenyl, thiobenzyl, thiomorpholinyl, morpholinyl, piperidinyl, an azacycloheptanyl, piperazinyl, pyrrolidinyl, pyrazolidinyl, and unsubstituted, monosubstituted, or disubstituted amino, wherein the amine substituents are selected from the group consisting of $(C_1-C_6)$ alkyl, $(C_3-C_7)$ cycloalkyl, phenyl, and benzyl,
with the proviso that of $R_1$ and $R_2$, and of $R_3$ and $R_4$, respectively, only one member of each pair is a strongly electron withdrawing group or a strongly electron donating group selected from subgroup A", G including the central spiro carbon atom represents a saturated or unsaturated ring with 5 to 8 carbon atoms of which at most one may be replaced with a hetero moiety selected from the group consisting of O, S, and NR$_5$, where R$_5$ has the meaning given above wherein at least one aromatic or heteroaromatic ring system selected from the group E is annellated to the ring G, wherein group E consists of benzene, naphthalene, phenanthrene, pyridine, quinoline, furan, thiophene, pyrrole, benzofuran, benzothiophene, indole, and carbazole, and wherein the ring system optionally may have one or more substituents from the group α defined above;

B and B' are independently selected from one of the groups a), b), c) and d) wherein
group a) consists of monosubstituted, disubstituted, and trisubstituted aryl selected from the group consisting of phenyl and naphthyl;
group b) consists of unsubstituted, monosubstituted and disubstituted heteroaryl selected from the group consisting of pyridyl, furanyl, benzofuran-2-yl, benzofuran-3-yl, thienyl, benzothieno-2-yl, benzothieno-3-yl or julolidinyl;
wherein the substituents of the aryl or heteroaryl in a) and b) are selected from the group consisting of hydroxy, amino, mono$(C_1-C_6)$ alkylamino, di$(C_1-C_6)$ alkylamino, mono- and diphenylamino wherein said mono- or diphenylamino is unsubstituted, monosubstituted, or disubstituted on the phenyl ring, piperidinyl, morpholinyl, carbazolyl, unsubstituted, monosubstituted, and disubstituted pyrryl, $(C_1-C_6)$ alkyl, $(C_1-C_6)$ alkoxy, bromine, chlorine, and fluorine, wherein the substituents of the phenyl or pyrryl are selected from the group consisting of $(C_1-C_6)$ alkyl, $(C_1-C_6)$ alkoxy, bromine, chlorine, and fluorine;
group c) consists of structural units having the formulas (V) or (W):

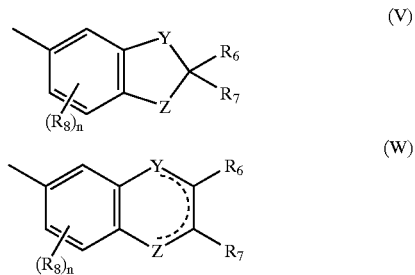

wherein Y and Z are independently selected from the group consisting of O, S, CH, CH$_1$ or NR$_9$, wherein R$_9$ is selected from the group D consisting of $(C_1-C_6)$ alkyl, $(C_1-C_6)$ acyl, phenyl and hydrogen; R$_6$ and R$_7$ independently represent hydrogen or $(C_1-C_6)$ alkyl; R$_8$ is a substituent selected from the subgroup A defined above, and n is 0, 1, 2 or 3;
with the proviso that if Y in formula (V) is NR$_9$, Z is carbon, and in group d) B and B' together form an unsubstituted, monosubstituted or disubstituted fluorene-9-ylidene radical or a saturated hydrocarbon radical, which is $C_3-C_{12}$ spiro-monocyclic, $C_7-C_{12}$ spiro-bicyclic or spiro-tricyclic, wherein the fluorene substituents are selected from the subgroup A.

2. A photochromic pyran compound according to claim 1, wherein G including the central spiro carbon atom is a substituted or unsubstituted fluorene, xanthene, thioxanthene, phenanthrene, or dihydroanthracene unit.

3. A photochromic pyran compound according to claim 1, corresponding to formula (II)

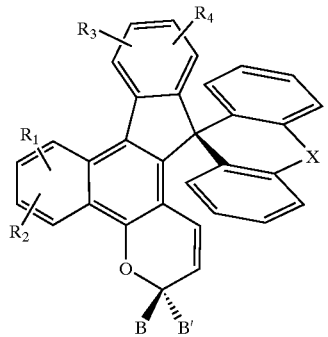

(II)

wherein X is —CR'$_2$—, —CR'=CR'—, —O—, —S— or a σ single bond, wherein the R' substituents are independently selected from the subgroup A.

4. A photochromic pyran compound according to claim 3, wherein R$_1$ and R$_2$ are attached in the 6-position and 7-position of the naphthopyran unit of formula II.

5. A photochromic pyran compound according to claim 1, wherein at most one of R$_1$ and R$_2$ and at most one of R$_3$ and R$_4$ is a strongly electron donating group.

6. A photochromic pyran compound according to claim 5, wherein, within the radical R$_1$ or R$_2$ and within the radicals R$_3$ or R$_4$, only one respectively is a strongly electron donating group.

7. A photochromic pyran compound according to claim 1, wherein the strongly electron donating group is independently selected from a morpholine group, a piperidine group, an azacycloheptane group, a piperazine group, a pyrrolidine group, a pyrazolidine group, and an unsubstituted, monosubstituted or disubstituted amino group, wherein the amine substituents may be selected from the group consisting of (C$_1$–C$_6$) alkyl, (C$_3$–C$_7$) cycloalkyl, phenyl and benzyl.

8. A photochromic pyran compound according to claim 1, selected from the group consisting of:
   spiro-9-fluorene-13'-[6-(N-morpholinyl)-3-[4-(N-morpholinyl)phenyl]-3-phenyl-indeno[2,1-f]-naphtho[1,2-b]pyran];
   spiro-9-fluorene-13'-[6-dimethylamino-3-[4-(N-morpholinyl)phenyl]-3-phenyl-indeno[2,1-f]-naphtho[1,2-b]pyran], and
   spiro-9-fluorene-13'-[6,11-bis(N-morpholinyl)-3-[4-(N-morpholinyl)phenyl]-3-phenyl-indeno[2,1-f]-naphtho[1,2-b]pyran].

9. An article of manufacture comprising a synthetic resin body and an effective color influencing amount of photochromic pyran compound according to claim 1.

10. An article of manufacture according to claim 9, wherein said synthetic resin body is an ophthalmic lens.

* * * * *